United States Patent [19]
Freed et al.

[11] Patent Number: 5,891,185
[45] Date of Patent: Apr. 6, 1999

[54] METHOD AND APPARATUS FOR TREATING OROPHARYNGEAL DISORDERS WITH ELECTRICAL STIMULATION

[75] Inventors: Marcy L. Freed, Pepper Pike, Ohio; Leonard A. Freed, Kailua, Hi.; Michael O. Christian, Beachwood, Ohio; Howard Tucker, Cleveland Heights, Ohio; Bernard Kotton, Beachwood, Ohio; Erol M. Beytas, Beachwood, Ohio; Marie Asmar, Richmond Heights, Ohio

[73] Assignee: ESD Limited Liability Company, Beachwood, Ohio

[21] Appl. No.: 966,580

[22] Filed: Nov. 10, 1997

Related U.S. Application Data

[63] Continuation-in-part of Ser. No. 549,046, Oct. 27, 1995, Pat. No. 5,725,564.

[51] Int. Cl.⁶ .................................................. A61N 1/18
[52] U.S. Cl. ............................................. 607/72; 607/62
[58] Field of Search ............................. 607/72, 39, 40, 607/62, 118, 63, 59

[56] References Cited

U.S. PATENT DOCUMENTS

| | | |
|---|---|---|
| 4,411,268 | 10/1983 | Cox . |
| 4,505,275 | 3/1985 | Chen . |
| 4,519,400 | 5/1985 | Brenman et al. . |
| 4,827,935 | 5/1989 | Geddes et al. . |
| 4,830,008 | 5/1989 | Meer . |
| 4,907,602 | 3/1990 | Sanders . |
| 5,016,647 | 5/1991 | Sanders . |
| 5,033,469 | 7/1991 | Brodard ........................ 607/48 |
| 5,755,745 | 5/1998 | McGraw et al. ................ 607/48 |

FOREIGN PATENT DOCUMENTS

| | | |
|---|---|---|
| A0036742 | 9/1981 | European Pat. Off. . |
| A0404427 | 12/1990 | European Pat. Off. . |
| WO9318820 A | 9/1993 | WIPO . |

OTHER PUBLICATIONS

H. Miki, W. Hida, T. Chonan, Y. Kikuchi, and T. Takishima, "Effects of Submental Electrical Stimulation During Sleep on Upper Airway Patency in Patients With Obstructive Sleep Apnea," American Review of Respiratory Disease, vol. 140, No. 5, pp. 1285–1289 (1989).

(List continued on next page.)

*Primary Examiner*—Scott M. Getzow
*Attorney, Agent, or Firm*—Covington & Burling

[57] ABSTRACT

A simple, non-invasive device and method for treating oropharyngeal disorders provides electrical stimulation to the pharyngeal region of a patient. Oropharyngeal disorders may cause an inability to swallow or difficulty in swallowing. The method and device provide an effective and non-invasive treatment for these disorders which is substantially more effective than traditional treatment methods, such as thermal stimulation. The method and device also effectively treat worst-case dysphagia (the inability to swallow) resulting from neurodegeneration and strokes. The device, an electrical pharyngeal neuromuscular stimulator, includes one or more pulse generators for generating a series of electrical pulses and a processor coupled to the pulse generators for controlling their operation. A switching network is also coupled to the pulse generators. The switching network directs series of electrical pulses respectively generated by the pulse generators to an electrode array positioned on the tissue of a patient's pharyngeal region. The processor controls the switching operation of the switching network by determining which electrode in the electrode array receives the series of pulses generated by the respective pulse generators. The electrode array also generates electrical feedback signals in response to the neuromuscular stimulation of the patient. The electrical feedback signals are provided to the processor via the switching network. The processor generates and stores test data and modifies the operation control signals and switching control signals in response to the electrical feedback signals.

16 Claims, 9 Drawing Sheets

OTHER PUBLICATIONS

Nicholas E, Diamant, "Firing Up The Swallowing Mechanism," Nature Medicine, vol. 2, No. 11, pp. 1190–1191 (Nov. 1996).

Shaheen Hamdy, Qasim Aziz, John C. Rothwell, Krishna D. Singh, Josephine Barlow, David G. Hughes, Raymond C. Tallis and David G. Thompson, "The Cortical Topography of Human Swallowing Musculature in Health And Disease," Nature Medicine, vol. 2, No. 11, pp. 1217–1224 (Nov. 1996).

METHOD AND APPARATUS FOR TREATING OROPHARYNGEAL DISORDERS WITH ELECTRICAL STIMULATION

RELATED APPLICATIONS

This application is a continuation-in-part of U.S. application Ser. No. 08/549,046, filed Oct. 27, 1995, and entitled "Method for Treating Dysphagia With Electrical Stimulation", now U.S. Pat. No. 5,725,564.

FIELD OF THE INVENTION

This invention relates to a method and apparatus for effectively treating oropharyngeal disorders. In particular, the present invention relates to a method and apparatus for treating oropharyngeal disorders by providing electrical stimulation to the pharyngeal region of an associated animal.

BACKGROUND OF THE INVENTION

Asymptomatic and symptomatic oropharyngeal disorders can lead to an inability to swallow or difficulty in swallowing. These disorders may be caused, for example, by stroke, neurodegenerative diseases, brain tumors or respiratory disorders.

Swallowing is a complicated action whereby food is moved from the mouth through the pharynx and esophagus to the stomach. The act of swallowing may be initiated voluntarily or reflexively but is always completed reflexively.

The act of swallowing occurs in three stages and requires the integrated action of the respiratory center and motor functions of multiple cranial nerves, and the coordination of the autonomic system within the esophagus. In the first stage, food or some other substance is placed on the surface of the tongue. The tip of the tongue is placed against the hard palate. Elevation of the larynx and backward movement of the tongue forces the food through the isthmus of the fauces in the pharynx. In the second stage, the food passes through the pharynx. This involves constriction of the walls of the pharynx, backward bending of the epiglottis, and an upward and forward movement of the larynx and trachea. Food is kept from entering the nasal cavity by elevation of the soft palate and from entering the larynx by closure of the glottis and backward inclination of the epiglottis. During this stage, respiratory movements are inhibited by reflex. In the third stage, food moves down the esophagus and into the stomach. This movement is accomplished by momentum from the second stage, peristaltic contractions, and gravity.

Although the main function of swallowing is the propulsion of food from the mouth into the stomach, swallowing also serves as a protective reflex for the upper respiratory tract by removing particles trapped in the nasopharynx and oropharynx, returning materials refluxed from the stomach into the pharynx, or removing particles propelled from the upper respiratory tract into the pharynx. Therefore, the absence of adequate swallowing reflex greatly increases the chance of pulmonary aspiration.

In the past, patients suffering from oropharyngeal disorders have undergone dietary changes or thermal stimulation treatment to regain adequate swallowing reflexes. Thermal stimulation involves immersing a mirror or probe in ice or another cold substance. The tonsillar fossa is stimulated with the mirror or probe, and the patient closes his mouth and attempts to swallow. While these traditional methods are usually effective for treating oropharyngeal disorders, in some patients these methods require that the patient endure weeks or months of therapy. It is also difficult to distinguish these patients who require more extensive treatments from patients who recover spontaneously. Thus, it is desirable to have a simple, non-invasive method and device for treating oropharyngeal disorders and artificially promoting swallowing which is effective within a relatively short treatment period.

Electrical stimulation has been used as a method for alleviating pain and stimulating nerves, as well as a means for treating disorders of the spinal cord or peripheral nervous system. Electrical stimulation has further been used to facilitate muscle reeducation and with other physical therapy treatments. In the past, electrical stimulation was not recommended for use in the neck because of the theoretical concerns that the patient would develop spasms of the laryngeal muscles, resulting in closure of the airway or difficulty in breathing. Further, the introduction of electrical current into the neck near the carotid body may cause cardiac arrhythmia.

More recently, electrical stimulation has been used to stimulate the recurrent laryngeal nerve to stimulate the laryngeal muscles to control the opening of the vocal cords to overcome vocal cord paralysis, to assist with the assessment of vocal cord function, to aid with intubation, and other related uses. There have been no adverse reactions to such treatment techniques. However, electrical stimulation has not been used in the treatment of oropharyngeal disorders to promote the swallowing reflex, which involves the integrated action of the respiratory center and motor functions of multiple cranial nerves.

SUMMARY OF THE INVENTION

The present invention provides a simple, non-invasive method and device for treating oropharyngeal disorders and artificially promoting swallowing. The method and device according to the present invention provide electrical stimulus to the pharyngeal region of a patient (a human or other animal) to stimulate muscles and nerves located in the pharyngeal region in order to promote swallowing.

The method and device for electrical pharyngeal neuromuscular stimulation according to the present invention are more effective for treating oropharyngeal disorders than traditional treatment methods, such as thermal stimulation. Further, the method and device of the present invention are effective for treating worst-case dysphagia resulting from neurodegeneration and strokes.

In particular, an apparatus according to the present invention includes one or more pulse generators for generating a series of electrical pulses and a processor coupled to the pulse generators for outputting operation control signals to the pulse generators. A switching network is coupled to the pulse generators and the processor. The switching network receives the series of electrical pulses from the pulse generators and outputs the series of electrical pulses in accordance with switching control signals received from the processor. An electrode array is also coupled to the switching network. The electrode array applies the series of electrical pulses output by the switching network to tissue of a pharyngeal region of a patient to achieve neuromuscular stimulation of the patient, and also generates electrical feedback signals in response to the neuromuscular stimulation of the patient. The electrical feedback signals are provided to the processor via the switching network. The processor generates and stores test data and modifies the operation control signals and switching control signals in response to the electrical feedback signals.

A method according to the present invention includes the steps of generating a series of electrical pulses using one or more pulse generators; generating operation control signals to control operation of the pulse generators; receiving the series of electrical pulses from the pulse generators at a switching network; generating switching control signals to control operation of the switching network; outputting the series of electrical pulses from the switching network in accordance with the switching control signals; applying the series of electrical pulses to the tissue of a pharyngeal region of a patient to achieve neuromuscular stimulation of a patient; generating electrical feedback signals in response to the neuromuscular stimulation of the patient; generating test data in response to the electrical feedback signals; and modifying the operation control signals and switching control signals in response to the electrical feedback signals.

These and other aspects of the invention will be apparent to those skilled in the art upon reading and understanding the specification that follows.

DETAILED DESCRIPTION OF THE PREFERRED EMBODIMENTS

Figure 1:
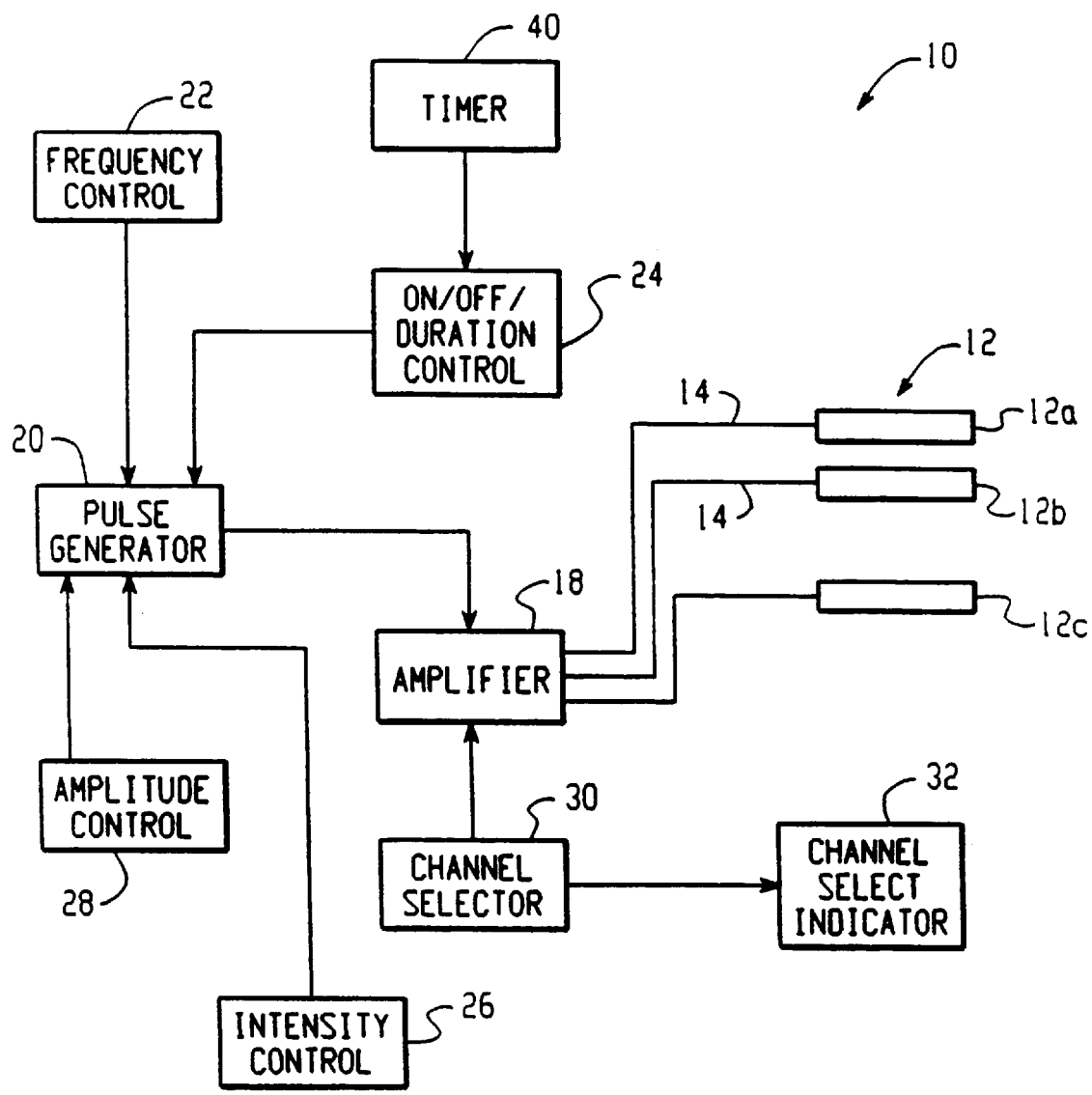
FIG. 1 is a diagram of an electrical pharyngeal neuromuscular stimulator according to the present invention for use in promoting swallowing.

The present invention will now be described in detail with reference to the accompanying drawings, which are provided as illustrative examples of embodiments of the invention only and not for purposes of limiting the same. In the drawings, like reference numerals indicate like elements throughout the several views.

FIG. 1 illustrates a first embodiment of an electrical pharyngeal neuromuscular stimulation device 10 for artificially promoting swallowing, wherein electrical stimulus is provided to the pharyngeal region of a patient to stimulate muscles located in the pharyngeal region in order to promote swallowing. The electrical pharyngeal neuromuscular stimulation device 10 as shown in FIG. 1 is comprised of a plurality of electrodes 12 (including individual electrodes 12a, 12b, and 12c) adapted to be selectively placed in electrical contact with tissue of a pharyngeal region of a patient and a pulse generator 20 for generating a series of electrical pulses in electrical contact with each of the plurality of electrodes 12.

The device 10 preferably includes at least two electrodes 12a and 12b, although three electrodes (12a, 12b, and 12c) are shown in FIG. 1. The electrodes 12a, 12b and 12c are preferably made of metal or some other physiologically acceptable conductive material. In general, the electrodes 12a, 12b and 12c are suitably any conventional and convenient shape that is suited for physiological applications. Lead wires 14 are attached to each electrode and are suitable for attachment to the pulse generator 20. Lead wires 14 may be made from any physiologically acceptable conductive metal, preferably insulated aluminum wire.

The series of electrical pulses is generated by selective control of pulse generator 20 which provides the series of electrical pulses to the plurality of electrodes 12 via an amplifier 18. Pulse generator 20 preferably includes a frequency controller 22 (shown as separate component in FIG. 1) which modulates an electrical signal generated by the pulse generator at a predetermined frequency to produce the series of electrical pulses output by the pulse generator 20. The frequency controller 22 may modulate the electrical signal at a fixed frequency, for example, 80 hertz, or may vary the frequency of the electrical pulses within a predetermined range of frequencies, for example, a range of frequencies from 4 to 80 hertz. Other frequency ranges as known in the art may also be used.

The pulse generator 20 also an on/off/duration control 24 for controlling the duration of time for which pulse generator 20 outputs the series of electrical pulses. The on/off duration control 24 may control pulse generator 20 to output the electrical pulses for a fixed duration, for example, a duration generally fixed at 300 microseconds. Alternatively, the on/off duration control 24 may control pulse generator 20 to output the electrical pulses for varying durations within a predetermined range, for example a range of 50 to 300 microseconds. Other durations as known in the art may also be used. The on/off duration control 24 may be adjusted manually or automatically using conventional circuits, such as a timer 40.

In the embodiment depicted in FIG. 1, the generator is further comprised of an intensity control circuit 26 (shown as a separate component in FIG. 1) for regulating the series electrical pulses such that the electrical current does not exceed a predetermined current value, for example, 25 milliamps RMS, and the power does not exceed a predetermined voltage value, for example, 9.6 MW RMS, or both. The intensity control circuit 26 limits the current and voltage values of the electrical pulses output by pulse generator 20 using conventional limiter circuits. The predetermined current and voltage values may vary in accordance with the patient's physical condition and tolerances and the treatments performed. The current applied should be sufficient to produce the desired response and promote the swallowing reflex. The intensity of the current is increased by small increments until the swallow response or muscle fasciculation occurs. However, the current that is applied should not be too intense in order to avoid laryngeal spasms or cardiac arrhythmia in the patient.

As depicted in FIG. 1, pulse generator 20 also includes an amplitude control circuit 28 (shown as a separate component in FIG. 1). Amplitude control circuit 28 allows for selective control of the amplitude of the electrical pulses generated by pulse generator 20 by manually or automatically operated conventional circuits as are known in the art.

A channel selector 30 suitably forms another input to amplifier to allow for concurrent activation of additional sets of electrodes (not shown) using conventional switching circuits. The status of channel selector 30 is indicated by a channel selector indicator 32.

In one embodiment of the present invention, the pulse generator 20 continuously generates electrical pulses for a predetermined period of time. Preferably, electric pulses are continuously generated and delivered to the electrodes until a complete swallow is achieved or the sensory tolerance level is reached in the patient. Additional treatments wherein the generator continuously generates electric pulses are suitably performed on the patient as necessary.

In an alternative embodiment of the present invention, the pulse generator 20 selectively generates cycles of electrical pulses. In this embodiment, pulse generator 20 is includes a treatment time control function which is accomplished with intensity control 26 in response to real time information provided by timer 40. The timer 40, intensity control 26, and pulse generator 16 also serve to provide functions of treatment time control, on-ramp control, and off-ramp control.

The treatment time control function selectively controls the duration of time wherein the pulse generator 20 selectively generates cycles of electric pulses. The treatment time is any suitable period, such as fifteen, thirty, or sixty minutes or continuous treatment. As with all settings, the particular values are highly application and patient specific. Thus, a suitable duration of the electric pulses in each cycle is manually or automatically set. In one embodiment according to the present invention, the duration of electric pulses in each cycle is within the range of 0.5 seconds to 30 seconds. Other durations as known in the art may also be used.

The treatment time control function also selectively controls the amount of time between each treatment cycle. For example, the treatment time control may be set to provide a delay between treatment cycles ranging from 0.1 seconds to 60 seconds. Other ranges as known in the art may also be used.

The on-ramp control function controls the amount of time required to reach the maximum intensity in each cycle. In one embodiment of the present invention, the amount of time required to reach the maximum intensity is between approximately 0.1 and 6.0 seconds. Other times as known in the art may also be used.

The off-ramp control function controls the amount of time required to decrease from the maximum intensity to zero intensity at the end of each cycle. In one embodiment of the present invention, the amount of time required to decrease from the maximum intensity to zero intensity is between approximately 0.1 and 6.0 seconds. Other times as known in the art may also be used.

A suitable commercially available device that provides the functions described above is a Staodyn® EMS+2 System manufactured by Staodyn, Inc. of Longmont, Colo.

Figure 2:
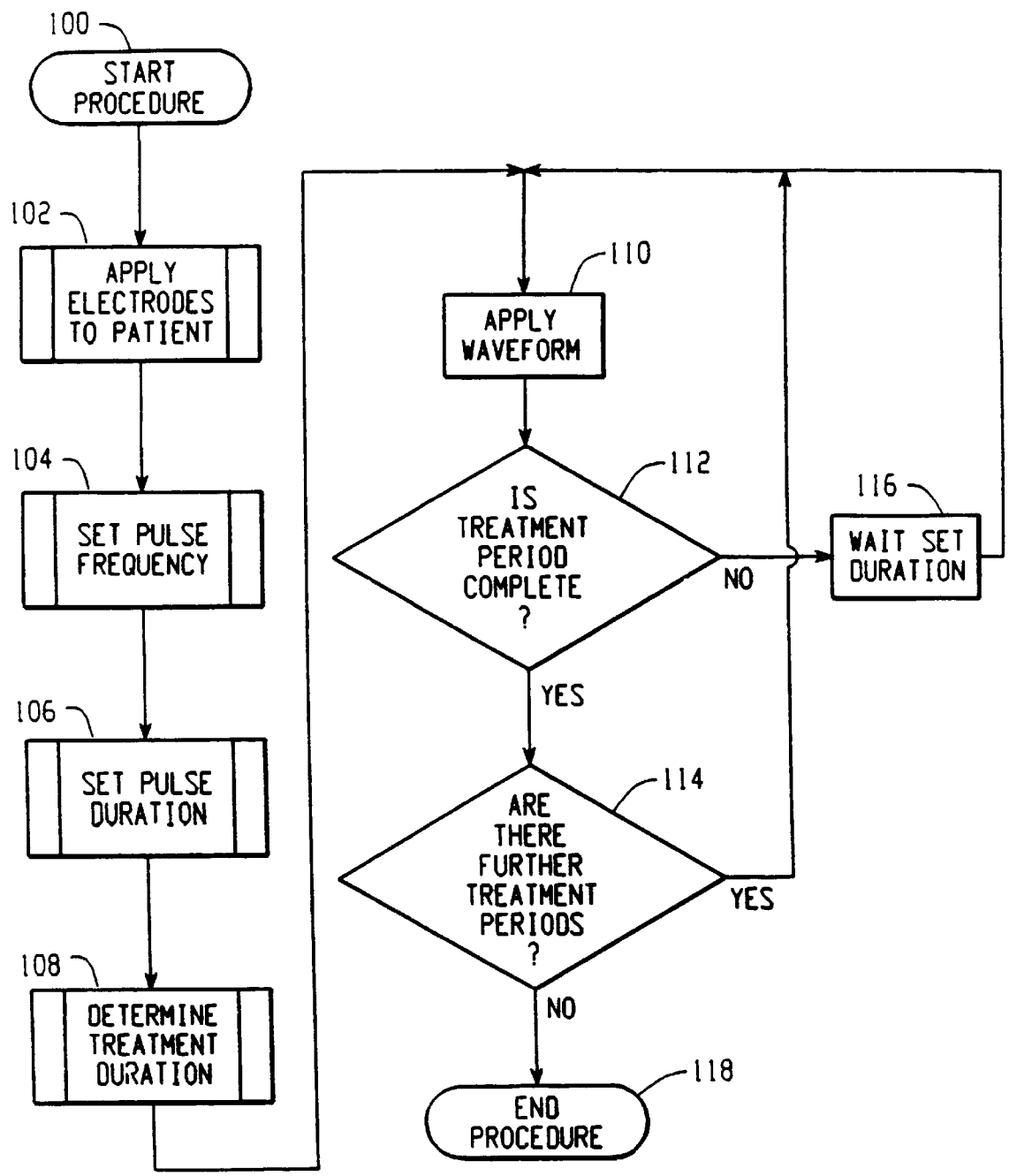
FIG. 2 is a flow chart of a method for electrical pharyngeal neuromuscular stimulation according to the present invention for promoting swallowing.

FIG. 2 provides a flow chart of a method for electrical pharyngeal neuromuscular stimulation according to the present invention. Turning to start procedure step 100, the procedure for treating oropharyngeal disorders with electrical stimulation is initiated. Next, at apply electrodes to patient step 102, actual electrodes are applied to the pharyngeal area of a patient. The particulars for electrode placement and selection are described in detail below with reference to FIGS. 3 and 4.

Turning next to set pulse frequency step 104, a pulse frequency is set in accordance with the parameters disclosed above. Similarly, at set pulse duration step 106, pulse duration is set. Finally, at determine treatment time step 108, a determination of a treatment duration is made, as well as to the number of treatment periods that are to be applied.

Turning next to apply waveform step 110, an actual waveform associated with the previously selected parameters is applied to the pharyngeal area of a patient. Next, at decision step 112, a determination is made as to whether a treatment period is complete in accordance with the preselected standards. A positive determination causes progress to decision step 114 and a negative determination causes progress to wait for duration step 116. At wait for duration step 116, the device automatically waits for a predetermined period of time before returning to apply waveform step 110.

At decision step 114, a determination is made as to whether further treatment periods are merited. A positive determination causes a return to wait set duration step 110. A negative determination results in completion of the treatment procedure as indicated by end procedure step 118.

An alternative embodiment of a device for electrical pharyngeal neuromuscular stimulation according to the present invention will now be described with reference to FIGS. 6 through 8.

Figure 6:
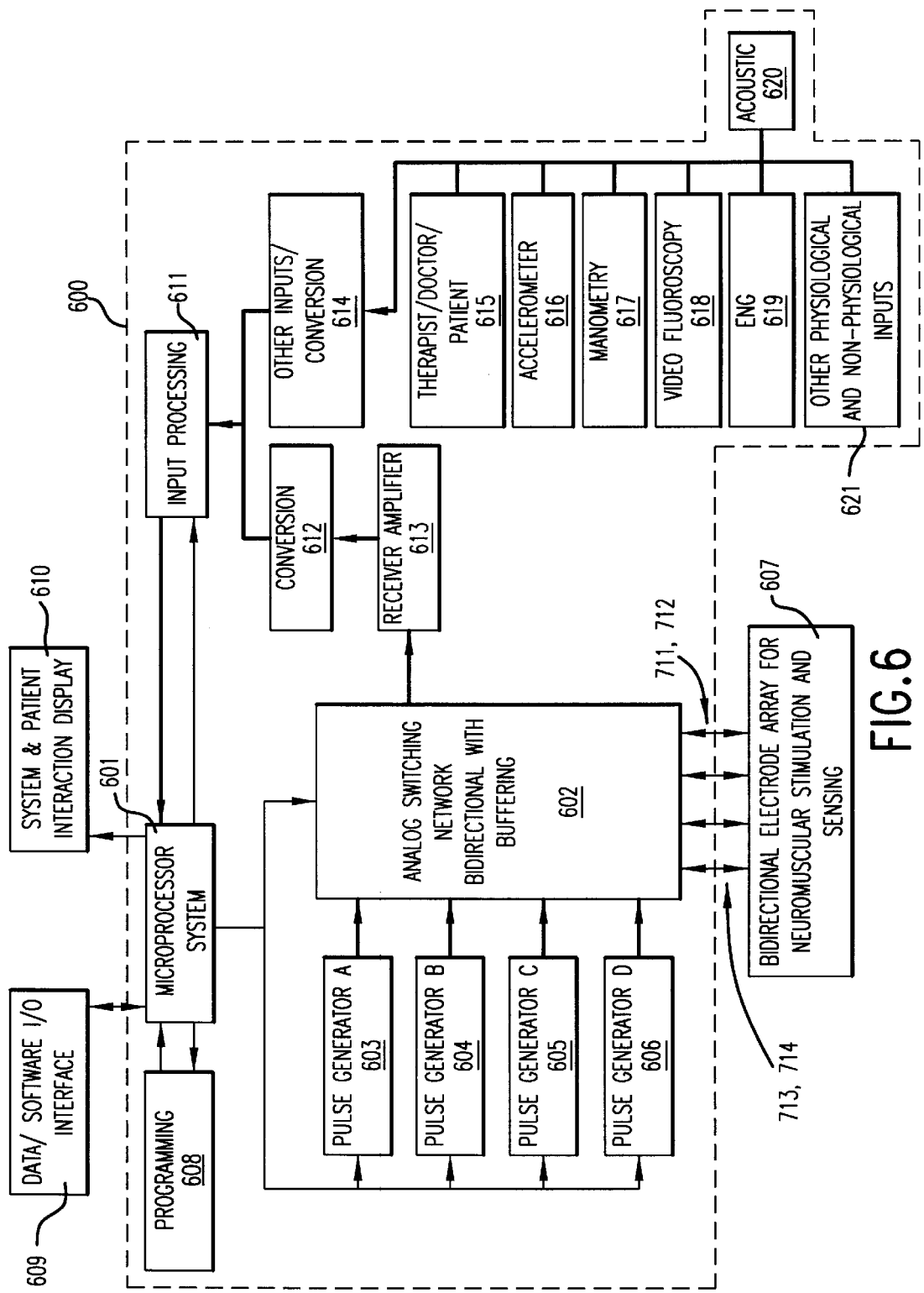
FIG. 6 is a block diagram of an alternative embodiment of an electrical pharyngeal neuromuscular stimulator according to the present invention, including a microprocessor system, a plurality of pulse generators, and a bi-directional analog switching network.

FIG. 6 illustrates a microprocessor-based stimulation device 600 including a microprocessor 601, a bi-directional analog switching network 602, and a plurality of pulse generators 603, 604, 605 and 606. Microprocessor 601 controls the operation of pulse generators 603 through 606 by generating control signals indicating the parameters for generation of electrical pulses for each pulse generator 603 through 606 respectively. For example, control signals provided by microprocessor 601 to each pulse generator 603 through 606 may include waveform, intensity, pulse width, ramp-on and ramp-off control signals. Upon receipt of the respective control signals from microprocessor 601, pulse generators 603 through 606 generate electrical pulses and output the pulses to bidirectional analog switching network 602.

Microprocessor 601 is also coupled to bidirectional analog switching network 602 and provides control signal to switching network 602 to control the operation of switching network 602 in processing and selectively outputting the electrical pulses to a bi-directional electrode array 607 coupled to switching network 602.

Switching network 602 receives electrical pulses generated by each of pulse generators 603 through 606. Based upon the control signals from microprocessor 601 to switching network 602 control, switching network 602 outputs the electrical pulses from one or more of pulse generators 603 through 606 to electrodes 710, 702, 703 and 704 (an exemplary arrangement of electrodes shown in FIG. 7) in electrode array 607 via lead wires 710, 711, 712, and 713 respectively. The control signals from microprocessor 601 to switching network 602 determine, for example, the sequence in which the electrical pulses from each of pulse generators 603 through 606 are provided to each electrode in electrode array 607 and the duration for which electrical pulses from each pulse generator will be provided to each electrode. Notably, switching network 602 may include one or more conventional buffer memories (not shown) to prevent overloading of the network.

According to one embodiment of the present invention, microprocessor 601, switching network 602 and pulse generators 603 through 606 may be designed to provide maximum flexibility of operation. Thus, each of the pulse generators may be capable of providing electrical pulses having either fixed or variable current and voltage values, modulation rates and frequencies. The wave form, intensity, and ramp-on and ramp-off functions provided by each pulse generator 603 through 606 may also be variably selected. Stimulation device 600 allows each of pulse generators 603 through 606 to independently produce simultaneous and/or sequential stimulation by each of the electrodes in electrode array 607.

In the preferred embodiment depicted in FIG. 6, microprocessor 601 is coupled to a programming device 608 which enables the microprocessor to be programmed to perform the processing functions in accordance with the present invention. Data may also be provided to microprocessor 601 by microprocessor vice 608. Programming of microprocessor 601 and downloading of data to the microprocessor may be accomplished through a conventional interface, such as standard RS232 serial and parallel ports or infrared links, as is known in the art.

Stimulation device 600 depicted in FIG. 6 also includes a feedback network for receiving and processing feedback received from electrode array 607. For example, electrode array 607 may use electromyographic (EMG) sensing capabilities to generate electrical feedback signals. The EMG sensing capabilities are utilized, for example, to determine whether muscles are contracting and, if so, the sequence of muscle contractions. This information is used to adjust the electrical pulses supplied to stimulate these muscles. Muscle contraction information may also be used to identify the patient's attempts to swallow, enabling the stimulator to facilitate the remainder of the swallowing sequence.

The feedback signals generated by electrode array 607 are provided to switching network 602 which outputs the feedback signals to a receiver amplifier 613. Receiver amplifier 613 amplifies the feedback signals and outputs the amplified feedback signals to a conversion circuit 612. Conversion circuit 612 formats the amplified feedback signals into a selected signal format and outputs the formatted feedback signals to an input processor 611. The selected signal format into which conversion circuit 612 converts the feedback signals is selected to enable input processor 611 to download and process the feedback signals.

In the preferred embodiment depicted in FIG. 6, input processor 611 also optionally receives one or more physiological and/or non-physiological inputs from input devices 615, 616, 617, 618, 619, 620 and 621. The physiological input devices such as devices 616, 617, 618, 619 and 620 provide inputs representing various physiological characteristics of the patient. For example, physiological inputs may be received from such devices as an accelerometer 616 (indicating motion due to a contraction of the muscle during swallowing), a manometry device 617 (indicating pressure increase due to the attempt at swallowing), a video fluoroscopy device 618 (for providing an input from visual examination of the patient's swallowing mechanism to determine the effectiveness of the swallow), an EMG device 619 (indicating additional muscle movements in the swallowing mechanism which may not be detected by the electrode stimulation patch), and/or an acoustic signaling device 620, e.g., a microphone placed on the neck of the patient, to detect swallowing sounds. The non-physiological devices such as device 615 provide inputs representing various non-physiological characteristics of the patient. Non-physiological inputs may be received from such sources as therapist/patient/doctor input device 615 which enables a therapist, patient and/or doctor to enter information such as the patient's threshold for the stimulation device parameters, including a minimum threshold needed and the maximum intensity usable for the patient, as well as parameters for altering the sequence and intensity of electrode stimulation for the patient based upon asymmetries which the patient may have during the swallowing process. Additional factors such as height, weight, neck thickness/size, pain tolerance, and the current status of the patient's ability to swallow may be entered for use in determining the appropriate stimulation frequency patterns and intensities. Additional physiological and/or non-physiological inputs may be received from other devices as indicated by representative input device 621.

The physiological and non-physiological inputs respectively generated by physiological and non-physiological input devices 615 through 620 are formatted by a conversion circuit 614 (similar to conversion circuit 612) and then stored and processed by input processor 611. Input processor 611 processes and stores as test data both the feedback signals originated by electrode array 607 and physiological and non-physiological inputs from devices 615 through 620. Input processor also receives control signals and data inputs from microprocessor 601.

In the preferred embodiment depicted in FIG. 6, a system and patient interaction display 610 is optionally provided. Display 610 is coupled to microprocessor 601 and receives processed data from input processor 611 via microprocessor 601. In this manner, display 610 enables monitoring of the feedback signals from electrode array 607 in addition to the status of inputs from the various physiological and non-physiological inputs 615 through 620 as described above. Display 610 may also enable monitoring of the operating status of stimulation device 600.

Generally, the display 610 may demonstrate, for example, current patient parameters, current inputs from the physiological and non-physiological devices and the electrode stimulation array, an overall rating of swallowing capability and current swallowing effectiveness, and the current setting (s) of the stimulation pattern frequency and/or intensity. Additionally, the display 610 may be adapted for monitoring by the patient to provide feedback to the patient as to how well swallowing has been completed. This feedback to the patient may assist with the patient's inherent bio-feedback mechanisms.

In the preferred embodiment depicted in FIG. 6, a data/software I/O interface 609 is optionally provided to enable downloading of testing data collected and processed by stimulation device 600, for example, during patient treatments. Patient-specific data may be downloaded to external devices, including portable devices, through any conventional interface (e.g., a hardwired interface, coaxial interface, infrared interface, etc.).

Figure 7:
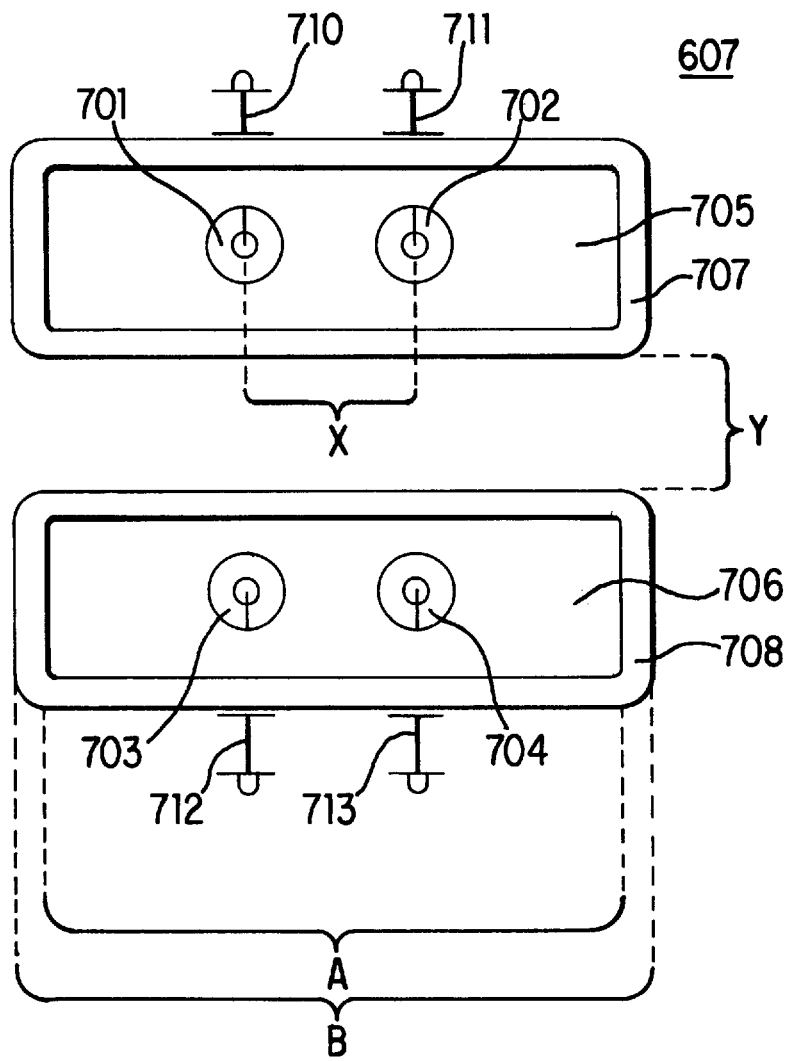
FIG. 7 is a diagram of an electrode array that may be used in conjunction with the embodiment of FIG. 6 to provide neuromuscular stimulation to a patient and to provide feedback signals to the bi-directional analog switching network of FIG. 6.

A preferred embodiment of a bi-directional electrode array 607 for use in conjunction with stimulation device 600 is illustrated in FIG. 7. Each bi-directional electrode in array 607 stimulates one or more pharyngeal muscles with electrical stimulation provided by the switching network 602, detects the electromyographic (EMG) response from the stimulated muscle(s), and provides the EMG response as an electrical feedback signal to the switching network 602.

Notably, the arrangement of electrodes and connecting wires shown in FIG. 7 is provided as an example and is not intended to limit the scope of the present invention. Unilateral electrodes (stimulating muscles but not sensing EMG signals from the stimulated muscles) may also be used in accordance with the present invention. Also, multiple electrodes, including squares of four, sixteen, twenty-five, or thirty-six electrodes or more, may be used. As the number of electrodes increases, the surface area treated by the array may be increased and/or the electrodes may be more closely positioned.

Figure 7A:
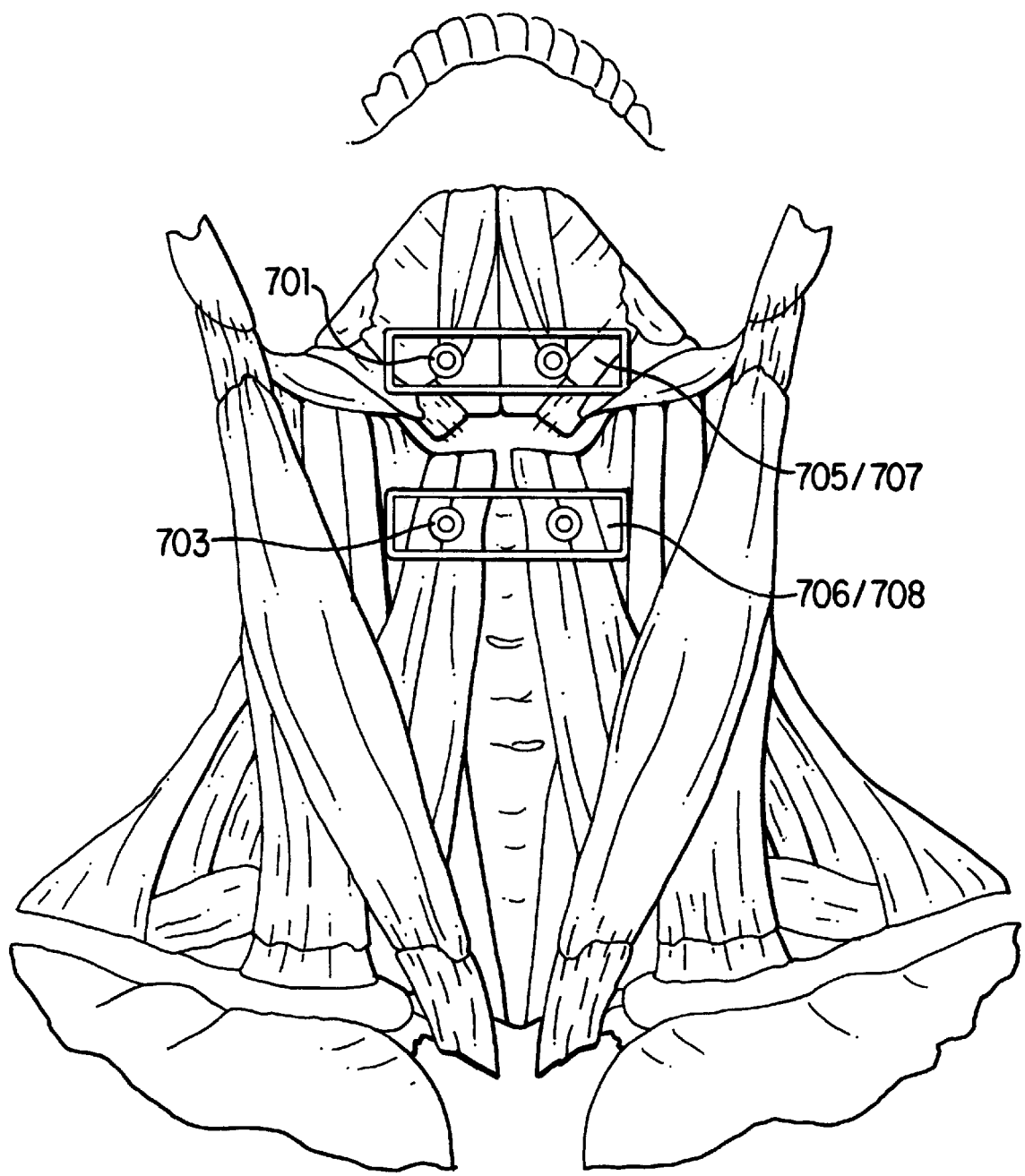
FIG. 7A illustrates the placement of an electrode array including four bi-directional electrodes on the pharyngeal region of a human patient.

As shown in FIG. 7, array 607 preferably comprises bi-directional four electrodes 701, 702, 703 and 704 which are positioned on the tissue of the pharyngeal region of a patient using adhesive bands 705 and 706 as illustrated in FIG. 7A. Each electrode 701–704 has a diameter of approximately two centimeters. The electrodes are arranged in two pairs. Each pair of electrodes is positioned such that the distance between the centers of the electrodes, shown as distance "X" in FIG. 7, is approximately three to four centimeters. The pairs of electrodes are spaced at a distance of approximately two and a half centimeters, shown as distance "Y" in FIG. 7.

The adhesive bands used to attach each pair of electrodes in array 607 to the patient have a width of approximately eight centimeters, shown as distance "A" in FIG. 7. Contact pads 707 and 708 having a width of approximately eight and a half centimeters (shown as distance "B" in FIG. 7) are also provided.

Each electrode of electrode array 607 is independently coupled to an output of switching network 602 (shown in FIG. 6) by lead wires 710, 711, 712, and 713 respectively. As a result, each electrode independently receives one or more series of electrical pulses generated by one or more of pulse generators 603–606 via switching network 602 as determined by microprocessor 601. Microprocessor 601 controls the switching operation of switching network 602 to control which output or outputs from pulse generators 603–606 are provided to each electrode in electrode array 607.

Figure 8:
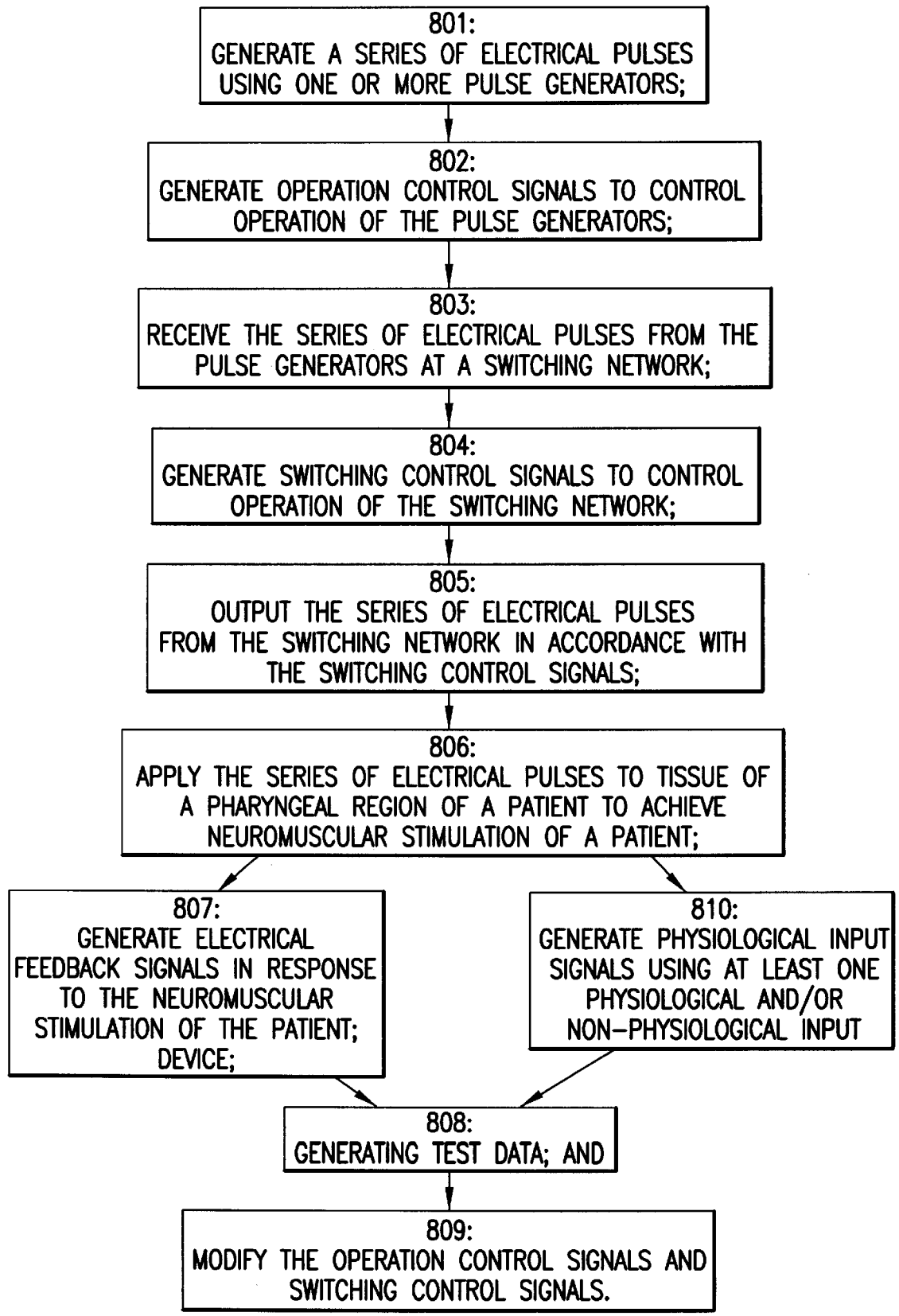
FIG. 8 is a diagram of an alternative method for electrical pharyngeal neuromuscular stimulation according to the present invention for promoting swallowing.

With reference to FIG. 8, an alternative embodiment of a preferred method for electrical pharyngeal neuromuscular stimulation according to the present invention includes the steps of:

801: generating a series of electrical pulses using one or more pulse generators;
802: generating operation control signals to control operation of the pulse generators;
803: receiving the series of electrical pulses from the pulse generators at a switching network;
804: generating switching control signals to control operation of the switching network;
805: outputting the series of electrical pulses from the switching network in accordance with the switching control signals;
806: applying the series of electrical pulses to tissue of a pharyngeal region of a patient using an electrode array to achieve neuromuscular stimulation of a patient;
807: generating electrical feedback signals in response to the neuromuscular stimulation of the patient;
808: generating test data in response to the electrical feedback signals; and
809: modifying the operation control signals and switching control signals in response to the electrical feedback signals.

This method may further include the step of:
810: generating physiological and/or non-physiological input signals using at least one physiological and/or non-physiological input device.

When step 810 is included, the test data generated in step 808 above is also based upon the physiological and/or non-physiological input signals. Similarly, step 809 above includes the modification of the operation control signals and switching of control signals in response to both the electrical feedback signals and the physiological and/or non-physiological input signals.

The preferred method depicted in FIG. 8 may optionally include the steps of monitoring the electrical feedback signals, the physiological input signals, the non-physiological input signals, or any combination thereof and downloading the test data to a test data receiver, for example, an external receiving device.

Several alternative two-electrode arrangements for the placement of electrodes on the tissue of the pharyngeal region of a patient will now be described in detail with reference to FIGS. 3 and 4. These arrangements are also provided as examples of electrode placement and are not intended to limit the number and arrangement of electrodes for use in practicing the present invention.

Figure 3:
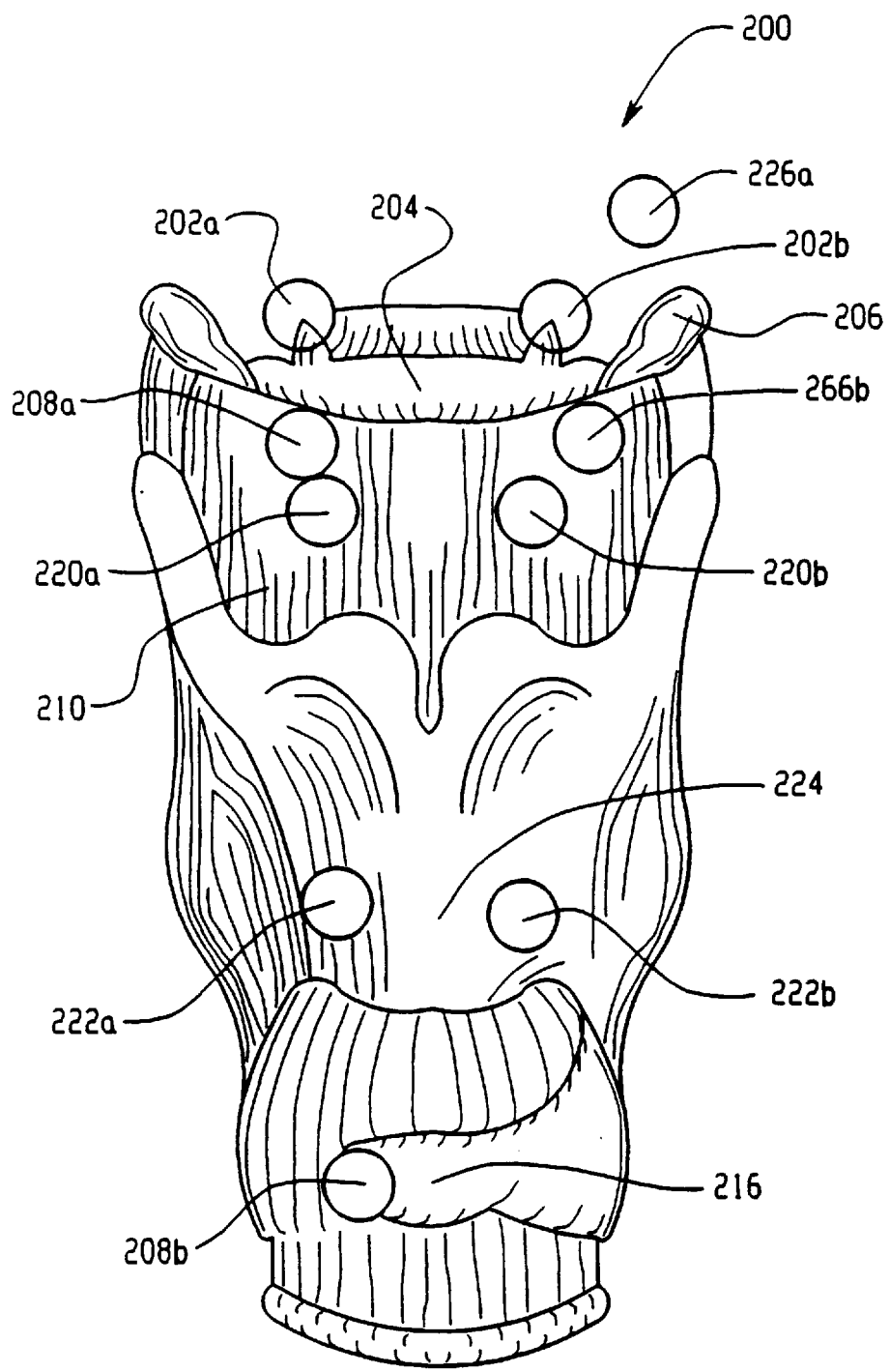
FIG. 3 is a view of a portion a pharyngeal region of a patient illustrating an exemplary placement of two electrodes according to the present invention.
Figure 4:
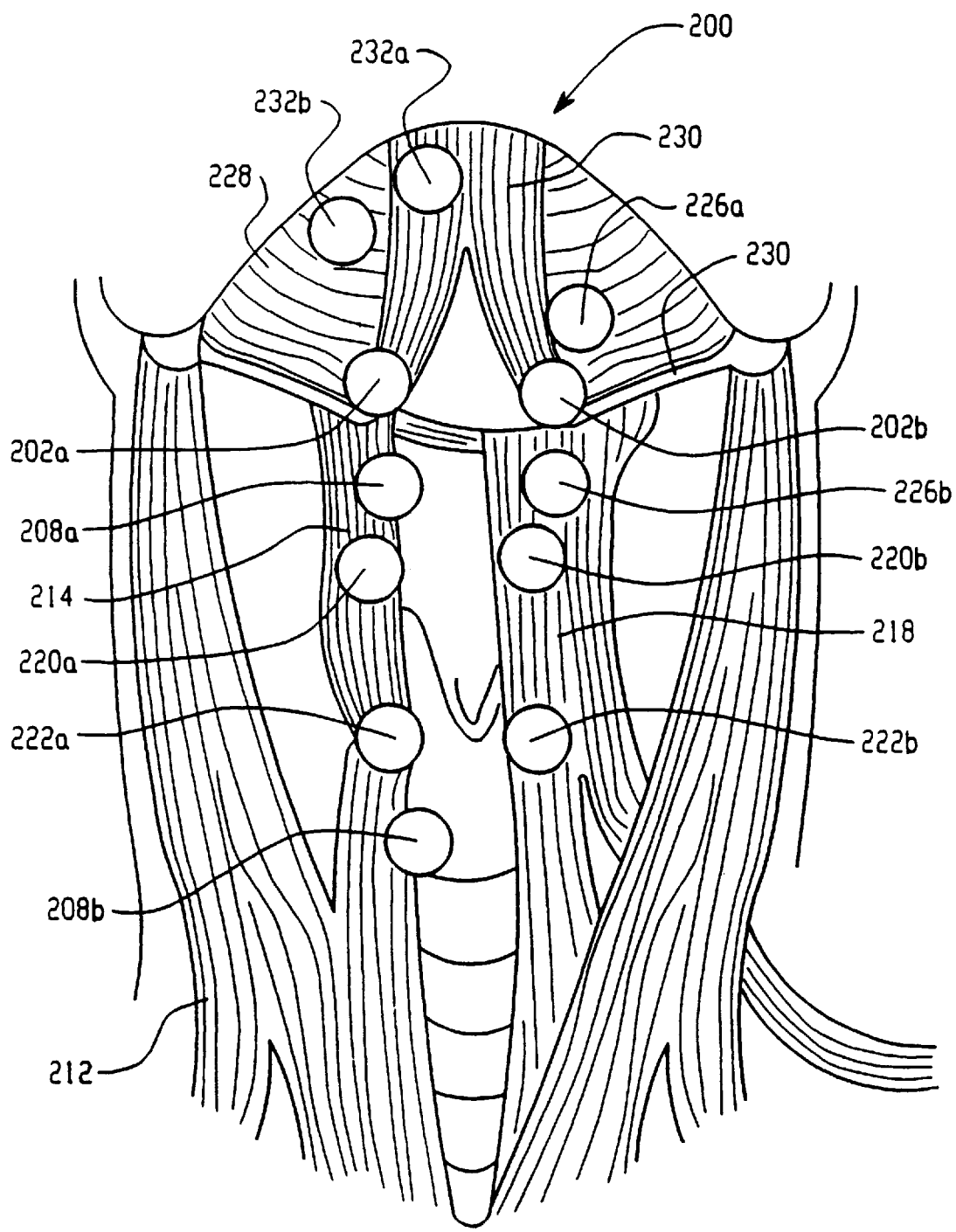
FIG. 4 is a view of a portion a pharyngeal region of a patient illustrating an exemplary placement of electrodes according to the present invention.

The electrodes are selectively placed in any suitable site within the pharyngeal region 200 of the patient as shown in FIGS. 3 and 4. The placement of the electrodes in the pharyngeal region of the patient is based on several factors, such as the extent and type of oropharyngeal disorder exhibited by the patient and, given the extent and type of oropharyngeal disorder exhibited, those locations within the pharyngeal region, when subjected to electrical stimulus, have the possibility of eliciting the strongest and most complete swallow. An evaluation for swallowing ability is done on the patient to determine the extent and type of oropharyngeal disorder. The critical elements in the evaluation are analysis by video fluoroscopy and clinical evaluation to determine the presence of a gag reflex, a dry swallow, and ability to tolerate one's own secretions. The placement of the electrodes may be changed several times in an effort to obtain the strongest and most effective treatment.

In a two-electrode embodiment of the present invention, a pair of electrodes 202 is positioned on the skin of the pharyngeal region 200 at approximately the position of the lesser horn 204 of the hyoid bone 206 on either side of the pharyngeal region 200 and just above the body of the hyoid bone 206. The electrodes overlie the muscles of the floor of the mouth (not shown).

In an alternative two-electrode embodiment of the present invention, a pair of electrodes 208 is positioned on the side of the pharyngeal region 200 on one side of the midline of the pharyngeal region 200. One electrode 208a is placed on the thyrohyoid membrane 210 at approximately the level of the lesser horn 204 close to the hyoid bone 206. This electrode 208a overlies the sternothyroid muscle 212 and the thyrohyoid muscle 214. The other electrode 208b is placed on the cricoid cartilage 216 to the side of the midline of the pharyngeal region 200. This electrode overlies the sternothyroid muscle 218 and the sternothyroid muscle 212 on one side of the midline of the pharyngeal region.

In another embodiment of the present invention, a pair of electrodes 220 is positioned on the skin of the pharyngeal region 200 on the thyrohyoid membrane 210 on either side of the midline of the pharyngeal region 200. These electrodes overlie the thyrohyoid muscle 214 and the sternothyroid muscle 218.

In yet another embodiment of the present invention, a pair of electrodes 222 is positioned on the skin of the pharyngeal region 200 on either side of the midline of the pharyngeal region 200 proximately midway between the thyroid notch 224 and the cricoid cartilage 216. These electrodes overlie the sternothyroid muscle 218 and the transition zone between the sternothyroid muscle 212 and the thyrohyoid muscle 214 on either side of the midline of the pharyngeal region 200.

In an additional embodiment of the present invention, a pair of electrodes 226 is positioned on the skin of the pharyngeal region 200 on one side of the midline of the pharyngeal region 200. One electrode 226a is placed just lateral to the lesser horn 204 of the hyoid bone 206 proximately midway between the hyoid bone 206 and the lower border of the mandible (not shown). This electrode overlies the mylohyoid muscle 228 and the digastric muscle 230. The other electrode 226b is placed proximate to the upper end of the thyrohyoid membrane 210 and proximate to the hyoid bone 206 or on the hyoid bone 206 proximately at the level of the lesser horn 204 of the hyoid bone 206. This electrode overlies the sternothyroid muscle 212 and the thyrohyoid muscle 214.

In a further embodiment of the present invention, a pair of electrodes 232 is positioned on the skin of the pharyngeal region 200 to the side of the midline of the pharyngeal region 200. One electrode 232a is placed on the midline of the pharyngeal region near the chin (not shown). The other electrode 232b is placed laterally to the other electrode. These electrodes overlie the mylohyoid muscle 228 and the digastric muscle 230 in the midline and to one side of the midline of the pharyngeal region 200.

In general, the placement and dimensions of the electrodes in accordance with the present invention is performed so as to avoid the carotid body and to insure the safety of the patient.

The practice of various embodiments of the method according to the present invention will now be described in detail. In the following examples, the inventive method was used to treat dysphagia.

EXAMPLE 1

One hundred and ninety-five patients suffering from dysphagia as a result of a stroke or neurodegeneration were studied. The swallowing ability of each patient was evaluated to determine the extent and type of dysphagia exhibited by the patient. The swallowing ability of each patient was assigned a number which corresponds to a defined swallow state wherein the swallow states are listed below: swallow state zero is the inability to have a pharyngeal contraction; swallow state one is the ability to swallow one's own secretions; swallow state two is the ability to swallow paste, pudding, or similar substances; swallow state three is the ability to swallow honey or similar substances; swallow state four is ability to swallow nectar or similar substances; swallow state five is the ability to swallow liquids; and swallow state six is the ability to swallow water. All of the patients were determined to have swallowing states of either zero or one, indicating the patient did not have a complete pharyngeal contraction and had no gag reflex or the ability to handle secretions. The patients were then objected to a series of treatment sessions. The patients were divided into two treatment groups: electrical stimulation and thermal stimulation.

Sixty three patients underwent a series of electrical stimulation treatment sessions. Preferably, the patients underwent a least seven electrical stimulation treatment sessions. In each treatment session, electrodes were selectively placed on the skin of the pharyngeal region of the patient. The placement of the electrodes was determined by the extent and type of dysphagia exhibited by the patient and, given the extent and type of dysphagia exhibited, those locations within the pharyngeal region, when subjected to electrical stimulus, have the possibility of eliciting the strongest and most complete swallow. Electrode placement was adjusted until the patient achieved the most complete swallowing contraction for which he was capable. Once the correct electrode placement was determined, the intensity of the current was increased by small increments until the tolerance and comfort level limits are reached in the patient. The optimal intensity was realized when the patient felt a tugging or pinch in the area of stimulation. The patient was then subjected to continuous electrical stimulation wherein electric pulses were continuously generated and delivered to the electrodes until a complete swallow was achieved or the tolerance level was reached in the patient. This step was repeated five to twenty times in each treatment session wherein the patient was subjected to continuous electrical stimulation. If the electrical stimulation was successful in promoting a complete contraction, swabbing of the oral cavity was done and the patient attempted a dry swallow. In those patients who did not exhibit any pharyngeal contraction, one or more treatment sessions were required before an adequate dry swallow occurred.

Once an adequate dry swallow was achieved, oral intake was provided to assist in the treatment. The consistency of the oral intake was determined by the strength of the contraction elicited by the patient. If the patient was able to swallow his own saliva, swabbing the oral cavity with a sponge moistened by water or juice was performed. The patient attempted to swallow the water or juice while subjected to continuous electrical stimulation. Once the patient had achieved audible, strong contractions, the patient was challenged with pudding, thick liquid, or ice slush. The patient attempted to swallow these substances while subjected to continuous electrical stimulation. Once three to five strong swallows were achieved with the assistance of electrical stimulation, the patient attempted to swallow these substances without the assistance of electrical stimulation. Treatment sessions continued with each patient until the patient's improvement plateaus.

Thirty-one patients were subjected to a series of thermal stimulation treatment sessions. Preferably, the patients were subjected to a least seven thermal stimulation treatment sessions. In each treatment session, a mirror or probe was immersed in ice or cold substance. The tonsillar fossa was stimulated with the mirror or probe. The patient then closed his mouth and attempted a dry swallow. If the stimulation was successful in promoting a complete contraction, oral intake was provided to assist in the treatment. The consistency of the oral intake was determined by the strength of the contraction elicited by the patient. Once an adequate dry swallow was achieved, oral intake was provided to assist in the treatment. The consistency of the oral intake was determined by the strength of the contraction elicited by the patient. If the patient was able to swallow his own saliva, swabbing the oral cavity with a sponge moistened by water or juice was performed. The patient attempted to swallow the water or juice while subjected to thermal stimulation. Once the patient had achieved audible, strong contractions, the patient was challenged with pudding, thick liquid, or ice slush. The patient attempted to swallow these substances while subjected to thermal stimulation. Once three to five strong swallows were achieved with the assistance of thermal stimulation, the patient attempted to swallow these substances without the assistance of thermal stimulation. Treatment sessions continued with each patient until the patient's improvement plateaus. Once the patient had achieved audible, strong contractions, the patient was challenged with pudding, thick liquid, or ice slush. The patient attempted to swallow these substances while subjected to continuous electrical stimulation. Once three to five strong swallows were achieved with the assistance of electrical stimulation, the patient attempted to swallow these substances without the assistance of thermal stimulation. Treatment sessions continued with each patient until the patient's improvement plateaus.

Figure 5:
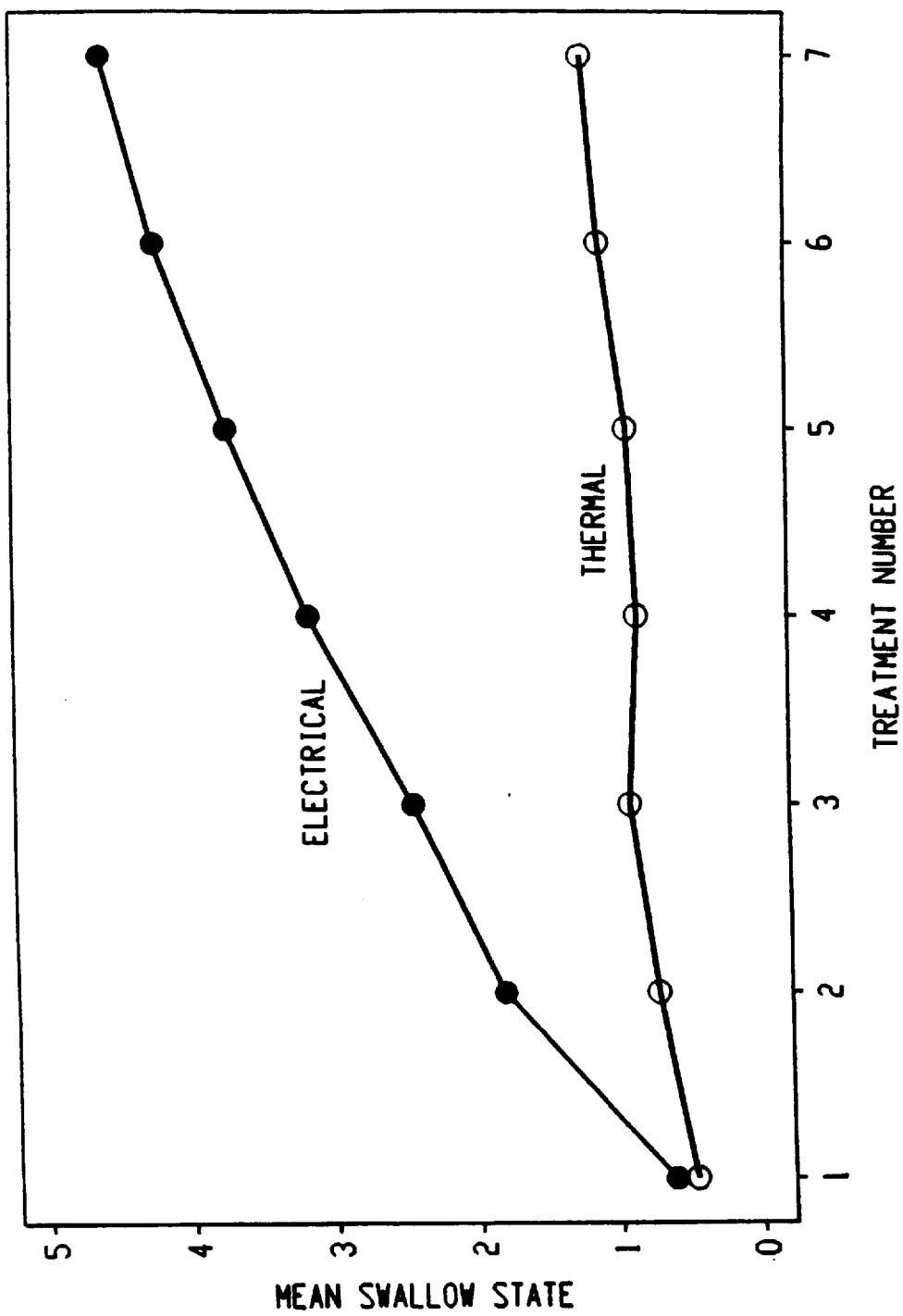
FIG. 5 is a graph illustrating the effectiveness of electric pharyngeal neuromuscular stimulation method and device according to the present invention.

The effectiveness of the electrical stimulation treatments and the thermal stimulation treatments is shown in FIG. 5. FIG. 5 is a graph illustrating the mean swallowing state achieved after electrical stimulation treatment sessions and thermal stimulation treatments. After seven treatment sessions, the mean swallowing state of the patients treated with electrical stimulation was swallow state five or the ability to swallow thin liquids. After seven treatment sessions, the mean swallowing state of the patients treated with thermal stimulation was only swallow state one or the ability to handle one's own secretions.

The method and device for electrical pharyngeal neuromuscular stimulation of the present invention provides an effective and non-invasive treatment for dysphagia. The method and device for electrical pharyngeal neuromuscular stimulation is more effective for treating dysphagia than traditional treatment methods, such as thermal stimulation. Further, the method and device of the present invention is effective for treating worst-case dysphagia resulting from neurodegeneration and strokes.

While various embodiments of a method and device for artificially promoting a swallowing reflex have been disclosed, it should be understood that modifications and adaptations thereof will occur to persons skilled in the art. Other features and aspects of this invention will be appreciated by those skilled in the art upon reading and comprehending this disclosure. Such features, aspects, and expected variations and modifications of the reported results and examples are clearly within the scope of the invention where the invention is limited solely by the scope of the following claims.

We Claims:

1. An electrical pharyngeal neuromuscular stimulator comprising:
    at least one pulse generator for generating a series of electrical pulses;
    a processor coupled to said at least one pulse generator for outputting operation control signals to said at least one pulse generator;
    a switching network coupled to said at least one pulse generator and said processor, said switching network receiving the series of electrical pulses from said at least one pulse generator and outputting, responsive to switching control signals from said processor, the series of electrical pulses; and
    an electrode array coupled to said switching network for applying the series of electrical pulses to tissue of a pharyngeal region of a patient to achieve neuromuscular stimulation of the patient, and for generating electrical feedback signals in response to the neuromuscular stimulation of the patient,
    wherein the electrical feedback signals are provided to said processor via said switching network, and
    wherein, in response to the electrical feedback signals, said processor generates and stores test data and modifies the operation control signals and switching control signals.

2. The electrical pharyngeal neuromuscular stimulator according to claim 1, wherein said switching network includes a buffer memory.

3. The electrical pharyngeal neuromuscular stimulator according to claim 1, further comprising at least one physiological input device for providing physiological input signals to said processor, wherein said processor modifies the operation control signals and switching control signals in response to the physiological inputs signals.

4. The electrical pharyngeal neuromuscular stimulator according to claim 3, further comprising a display device coupled to said processor for monitoring at least one of the electrical feedback signals, physiological input signals, test data, and operating status of said pharyngeal neuromuscular stimulator.

5. The electrical pharyngeal neuromuscular stimulator according to claim 1, further comprising at least one non-physiological input device for providing non-physiological input signals to said processor, wherein said processor modifies the operation control signals and switching control signals in response to the non-physiological inputs signals.

6. The electrical pharyngeal neuromuscular stimulator according to claim 5, further comprising a display device coupled to said processor for monitoring at least one of the electrical feedback signals, non-physiological input signals, test data, and operating status of said pharyngeal neuromuscular stimulator.

7. The electrical pharyngeal neuromuscular stimulator according to claim 1, further comprising a programming device coupled to said processor for transmitting programming information and data to said processor.

8. The electrical pharyngeal neuromuscular stimulator according to claim 1, further comprising a data/software interface device coupled to said processor for transmitting the test data.

9. The electrical pharyngeal neuromuscular stimulator according to claim 1, wherein said electrode array comprises four bi-directional electrodes.

10. The electrical pharyngeal neuromuscular stimulator according to claim 1, wherein said electrode array comprises four uni-directional electrodes.

11. A method for electrical pharyngeal neuromuscular stimulation for artificially promoting swallowing, comprising the steps of:
    generating a series of electrical pulses using at least one pulse generator;
    generating operation control signals to control operation of said at least one pulse generator;
    receiving the series of electrical pulses from said at least one pulse generator at a switching network;
    generating switching control signals to control operation of said switching network;
    outputting the series of electrical pulses from said switching network in accordance with said switching control signals;
    applying the series of electrical pulses to tissue of a pharyngeal region of a patient using an electrode array;
    generating electrical feedback signals in response to the application of the series of electrical pulses;
    generating test data in response to the electrical feedback signals; and
    modifying the operation control signals and switching control signals in response to the electrical feedback signals.

12. The method for electrical pharyngeal neuromuscular stimulation according to claim 11, further comprising the step of generating physiological input signals using at least one physiological input device; wherein the test data is generated in response to the electrical feedback signals and the physiological input signals; and wherein the operation control signals and switching control signals are modified in response to the electrical feedback signals and the physiological inputs signals.

13. The method for electrical pharyngeal neuromuscular stimulation according to claim 12, further comprising the step of monitoring of the electrical feedback signals and the physiological input signals.

14. The method for electrical pharyngeal neuromuscular stimulation according to claim 11, further comprising the step of generating non-physiological input signals using at least one non-physiological input device; wherein the test data is generated in response to the electrical feedback signals and the non-physiological input signals; and wherein the operation control signals and switching control signals are modified in response to the electrical feedback signals and the non-physiological inputs signals.

15. The method for electrical pharyngeal neuromuscular stimulation according to claim 14, further comprising the step of monitoring of the electrical feedback signals and the non-physiological input signals.

16. The method for electrical pharyngeal neuromuscular stimulation according to claim 11, further comprising the step of downloading the test data to a test data receiving device.

* * * * *